United States Patent [19]

McAbery

[11] 4,321,215

[45] Mar. 23, 1982

[54] PROCESS FOR EXTRACTION AND NEUTRALIZATION OF HYDROCARBON SULFONIC ACIDS

[75] Inventor: James W. McAbery, Elmhurst, Ill.

[73] Assignee: Standard Oil Company (Indiana), Chicago, Ill.

[21] Appl. No.: 911,365

[22] Filed: Jun. 1, 1978

[51] Int. Cl.³ .................. C07C 139/00; C07C 143/24
[52] U.S. Cl. ......................... 260/504 S; 260/504 R; 260/505 P; 260/513 R
[58] Field of Search ............ 260/504 S, 505 P, 513 R, 260/504 R

[56] References Cited

U.S. PATENT DOCUMENTS

| | | | |
|---|---|---|---|
| 1,868,596 | 7/1932 | Elchwald | 260/504 S |
| 2,223,194 | 11/1940 | Thompson | 260/504 S |
| 3,225,086 | 12/1965 | Sias et al. | 260/504 S |

*Primary Examiner*—Alan Siegel

*Attorney, Agent, or Firm*—Mark J. DiPietro; William T. McClain; William H. Magidson

[57] ABSTRACT

A method for producing ammonium hydrocarbon sulfonate which comprises (1) contacting a sulfonation liquor comprising a hydrocarbon sulfonic acid, unreacted hydrocarbon, and $SO_3$ with an alcoholic extraction medium in which the unreacted hydrocarbon is insoluble, (2) separating the insoluble hydrocarbon raffinate from the extraction medium, (3) removing a substantial portion of the extraction medium in a stripping tower to produce a hydrocarbon sulfonic acid having a residual amount of extraction medium, (4) neutralizing the hydrocarbon sulfonic acid with an excess of ammonia to produce an ammonia hydrocarbon sulfonate and heating the ammonium hydrocarbon sulfonate to remove residual volatile material. To conserve ammonia and solvent, this volatile material is returned to the stripping tower.

6 Claims, 1 Drawing Figure

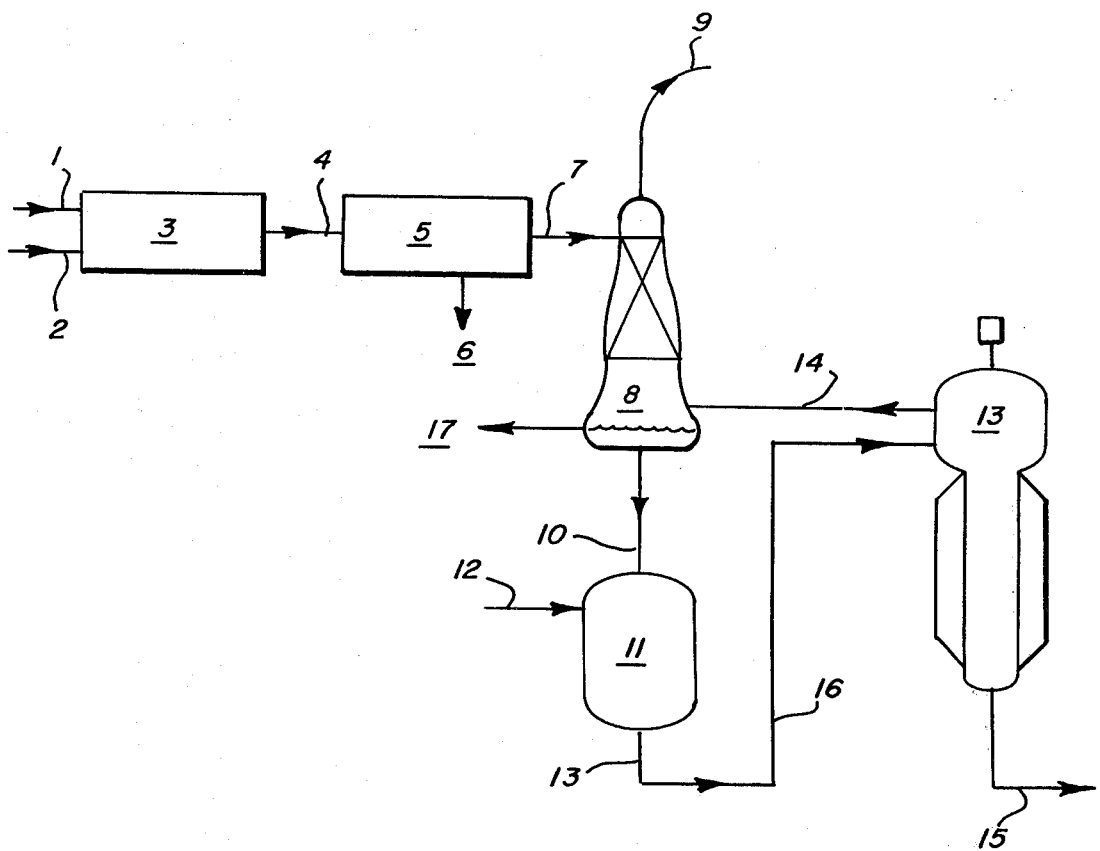

PROCESS FOR EXTRACTION AND NEUTRALIZATION OF HYDROCARBON SULFONIC ACIDS

This invention relates to the purification of sulfonation liquors containing a crude sulfonated hydrocarbon or hydrocarbon sulfonic acid. More particularly this invention relates to an improved purification process for sulfonated hydrocarbon liquors which improves yield, prevents corrosion and conserves energy, extraction media and ammonia.

There has been considerable interest in recent years in sulfonation processes for producing ammonium hydrocarbon sulfonate. Many of these processes have problems implicit in the purification of the ammonium hydrocarbon sulfonate (sulfonated hydrocarbons). In general two types of purification schemes are used. In the first scheme the extraction medium is removed from the unneutralized sulfonic acid and the acid is then neutralized with ammonia. In the second scheme the extraction medium is removed from the neutralized ammonium sulfonate.

The first purification scheme suffers from corrosion and the second suffers from inefficient, incomplete extraction. In the first purification scheme, when the crude extraction medium-unneutralized sulfonic acid stream is passed into an extraction medium stripper, the corrosive unneutralized acid quickly corrodes metallic strippers. Substantially complete extraction medium removal is required in single stage stripping. Thus, extended residence times and intimate contact with metallic vessel surfaces are necessary to maximize heat transfer. Solvent recovery systems clad with metallic corrosion resistant materials can be used but are expensive and also suffer lesser but significant corrosion. Solvent strippers clad with non-metallic corrosion resistant materials are unsuitable. The nonmetallic strippers are inefficient, remove less than an adequate amount of solvent because of less efficient heat transfer, are expensive and are also subject to lesser but significant rates of corrosion. The corrosion of the solvent separator systems causes plant shut-downs and problems with harmful metallic corrosion product impurities such as iron in the ammonium sulfonate product. Replacement of vessels ruined by corrosion is also very expensive.

In the second conventional scheme, the hydrocarbon sulfonic acid is neutralized with excess ammonia and then stripped of extraction media. When the sulfonic acid is stripped with excess ammonia present, the ammonia stripped with the extraction medium is recycled to the extractor. The corrosion problems are minimal. The neutralized ammonium sulfonate is less corrosive than sulfonic acid. However, problems are caused by ammonia present in the extraction medium. The ammonia increases the pH, or basicity of the extraction medium and retards the extraction-phase separation of the unreacted hydrocarbon raffinate phase from the extraction medium containing the sulfonic acid phase. This retarded phase separation causes lowered sulfonic acid yields. Also, this inefficient phase separation leaves a small but harmful amount of unreacted hydrocarbons in the sulfonic acid. Purer, more stable products with significantly better performance in tertiary oil recovery are formed if the sulfonic acid is substantially free of unreacted hydrocarbons.

These processes also have the drawbacks that they require relatively large waste ammonia disposal facilities and consume large amounts of heat, ammonia and extraction solvent.

Accordingly there is a need for a process which conserves ammonia and heat, does not pose corrosion problems, does not pose inefficient extraction-phase separation problems, and increases production of sulfonic acid.

The principal object of the present invention is to provide an improved method for the extraction, neutralization and purification of sulfonic acid and recovery of the extraction medium in the production of ammonium sulfonate. Another object of this invention is to prevent extraction-phase separation problems caused by the recycle of ammonia with the recovered extraction medium to the extractor. Another object of the invention is to prevent the corrosion of extraction medium strippers.

Other objects of the invention are to reduce ammonia and extraction medium consumption, and lower the contamination of the environment with ammonia, to increase the production of sulfonic acid and to reduce heat consumption to conserve fuel. Other objects of the invention will become apparent to those skilled in the art upon the reading of the specification and claims.

The objects in this invention can be attained by a method for producing ammonium hydrocarbon sulfonate which comprises (1) contacting a sulfonation liquor comprising a hydrocarbon sulfonic acid, unreacted hydrocarbon, and $SO_3$ with an alcoholic extraction medium in which the unreacted hydrocarbon is insoluble, (2) separating the insoluble hydrocarbon raffinate from the extraction medium, (3) removing a substantial portion of the extraction medium in a stripping tower to produce a hydrocarbon sulfonic acid having a residual amount of extraction medium, (4) neutralizing the hydrocarbon sulfonic acid with an excess of ammonia reagent to produce an ammonium hydrocarbon sulfonate and heating the ammonium sulfonate to remove residual volatile material. To conserve ammonia and solvent, this volatile material is returned to the stripping tower.

In contrast to conventional purification schemes where the crude extract of the sulfonation liquor is neturalized either prior to or subsequent to a one stage stripping of the extraction medium, my process entails removing a substantial amount of the solvent from the crude extract of the sulfonation liquor, neutralizing the sulfonic acid and removing substantially all of the remaining extraction medium and other volatiles. In this way the extraction-phase separation efficiency is not harmed by pH control problems caused by ammonia being recycled to the extraction. The bulk of the extraction medium is stripped prior to neutralization with ammonia, and the balance of the medium is scrubbed of ammonia in the tower upon recycle from the final stripping. The corrosion problems are prevented by an initial stripping of the extraction medium in a packed tower where complete one stage stripping is not needed and thus extended intimate contact of acid with metallic surfaces does not occur.

The final stripping of the neutralized ammonium sulfonate can occur using high temperature contact of the non-corrosive ammonium sulfonate with metallic surfaces to remove substantially all of the extraction media. This stripping of the ammonia sulfonate avoids the high temperature of degradation temperature sensitive free acid, and promotes essentially full recovery of extraction medium. The stripped volatiles contain ammonia and extraction media which can be conserved by returning the volatiles to the stripping tower, where the ammonia is stripped from the extraction medium and conserved by the free sulfonic acid therein.

Advantages, other than the prevention of corrosion and elimination of ammonia in extraction media recycle, are inherent in this invention. Ammonia is consumed at a lower rate with the same production of ammonium sulfonate. The ammonia stripped in the reboiler is recycled along with extraction media to the stripping tower. In the tower the excess ammonia, which is ordinarily waste ammonia, reacts with the sulfonic acid and is conserved as ammonium sulfonate. This ammonia neutralization eliminates much ammonia waste and eliminates the need to provide a large waste treatment facility for ammonia. The recycle prevents ecological damage from ammonia waste and provides substantially complete utilization of ammonia.

The neutralization reaction between ammonia and sulfonic acid is exothermic, i.e., produces heat energy. This heat energy is conserved in the invention to reduce heating needed in the reboiler stripping step. The heat released by the neutralization reaction remains in the ammonium sulfonate and reduces heating needed to vaporize the excess ammonia, water and extraction medium in the final stripping. This utilization of inherent chemical heating saves fuel.

With reference to the drawing in FIG. I, crude sulfonated hydrocarbon liquor flows through 1, and alcoholic extraction medium flows through 2 into the extractor 3. In the extractor 3, the extraction medium dissolves, extracts and separates the sulfonic acid from the insoluble unreacted hydrocarbons. The extraction medium and sulfonation liquor flow through 4 into extraction 5. The insoluble unreacted hydrocarbon raffinate is removed from the extractor through 6, and the extraction medium containing the sulfonic acid passes through 7 into the stripping column 8. The column is stripped with a heated gaseous stream through 17 and the stripped medium passes out 9 to be recovered. The partly stripped sulfonic acid passes through 10 into the ammonia reactor 11 to be neutralized. Ammonia reagent passes into the reactor through 12. The neutralized ammonium sulfonate passes through 16 with excess ammonia into the reboiler 13 where the residual ammonia, water and extraction medium are stripped, and sent through 14 to the tower 8 where the ammonia is removed by reaction with the sulfonic acid. The purified ammonium sulfonate is removed through 15.

After extraction the crude sulfonic acid and extraction medium stream at about 2000-5000 pounds per hour is passed into a fractionating solvent stripper. This fractionating tower is heated to a temperature which will vaporize the extraction medium or aqueous alkanol water azeotrope in the case of aqueous media. The tower may be heated by any means which will maintain a temperature sufficient to evaporate the extraction medium such as heated gas stream of nitrogen or steam. Preferably, for reasons of economy and ease of handling, steam heating is preferred. For isopropanol water systems, the boiling point of the azeotrope is about 100° F. at 2 psia to 300° F. at 150 psia other alcohol systems have similar properties. The steam is injected into the tower and is passed counter current to the sulfonic acid inside the tower stripping the extraction medium and condensing water. About 1000-3000 pounds per hour of extraction medium condenses overhead. Typically the stripped hydrocarbon sulfonic acid contains about 15.0 to 1.0 weight percent extraction medium.

The selective evaporation of the extraction media components is promoted by a tower packing. This packing is acid resistant and can be made from materials such as plastic, graphite, ceramic, acid resistant alloys, etc. Plastics such as polyethylene, polypropylene, and "Teflon," "Kynar" can be used. The purpose of the packing is to increase the surface area of the extraction medium to promote evaporation of the extraction medium or of the more volatile component of the extraction medium if a mixture is used.

The tower is protected from corrosion by being constructed from non-metallic materials or by a nonmetallic lining.

About 2000-6000 pounds per hour of the sulfonic acid (about 33% active) containing residual extraction medium, oil, and water from the steam condensate passes into a neutralizer from the tower bottoms. In the neutralizer the sulfonic acid is contacted with from about a neutralizing amount of ammonium to about a 50% molar excess of an ammonia-containing neutralizing agent from at about 100 to 200 pounds per hour based on ammonia which provides an excess of ammomia to neutralize the sulfonic acid. The rate of ammonia can be adjusted to provide a pH between 5-8 preferably 6-7. The excess ammonia is carried along in the sulfonic acid. The ammonia-containing neutralizing agent may be liquid ammonia or 100 percent gaseous ammonia or an aqueous solution of ammonia, or mixtures thereof. The neutralizer must contain means such as baffles or rotors to thoroughly mix the ammonia stream with the sulfonic acids stream to promote complete neutralization. The residence time within the neutralizer must be sufficient to obtain complete neutralization. The neutralization reaction is rapid at temperatures present in the neutralizer and the residence time is generally less than a minute, often less than 10 seconds.

The neutralized sulfonic acid contains residual amounts of extraction medium and water and ammonia. This water results from either the neutralization reaction, from steam stripping condensate, from an aqueous extraction medium or from the sulfonation reaction. The partly stripped neutralized sulfonate passes into a final extraction medium stripping vessel or reboiler. In the reboiler the sulfonic acid is heated to a temperature, generally about 220° F. to 400° F. sufficient to substantially remove the extraction medium, ammonia and residual water left from the process. It is not critical to this invention that the reboiler be of any specific configuration, any common heating means which is sufficient to remove extraction medium and water is sufficient. Examples of commonly used apparatus are shell and tube heat exchangers thin film evaporators commercially called "Votator" mechanism, or continuously stirred pots. In the reboiler the sulfonate is heated to a temperature to drive off excess ammonia, residual extraction medium and water.

This ammonia, extraction and water stream is recycled to the tower, wherein the ammonia is scrubbed from this stream by the sulfonic acid materials which are there being stripped of extraction medium. The ammonia stripped from the stream is recovered in this way through reaction with the sulfonic acid and is recycled in the system in aiding in neutralization of the acid. The water and extraction medium is recovered and water content can be removed or adjusted prior to recycle of the extraction medium to the extractor. The ammonium sulfonate is recovered from the bottoms of the reboiler.

Hydrocarbon streams which can be sulfonated and purified in this method are petroleum fractions, crude oils, gas oils, lubricant oil fractions, bright stocks, alkylated benzene compounds, etc. Preferably for reasons of economy and ease of sulfonation gas oils, hydrogenated gas oils and crude oils are preferably sulfonated with this process to produce materials for tertiary oil recovery chemicals.

Extraction media which may be used in the extraction of the crude sulfonic acid from the unreacted hydrocarbon are lower alkanols, such as methanol, ethanol, propanol, isopropanol and butanol, and mixed aqueous-lower alkanol media. Preferably isopropanol is used for reasons of economy and efficiency in extraction of the sulfonic acid from the mixture. Aqueous media can be used, for example, mixed solvents of alkanols and water. Alkanols with greater than 4 carbon atoms have limited solubility in water and are not used. isopropanol-water mixed media has 0.2-100 parts, preferably 0.5-2.0 parts water per part of isopropanol. The mixed aqueous-alcohol extraction media are preferred due to the low solubility of unreacted hydrocarbons in the media.

EXAMPLE I

The process in FIG. I can be operated as follows: sulfonation liquor at 100° F. enters the extractor at a rate of 5000 pounds per hour of sulfonic acid, oil, sulfur trioxide, hydrocarbon, and other impurities. The extraction media in a weight ratio of 1800 parts of water and 1200 parts of isopropanol is contacted with the sulfonation liquor at a rate of 3000 pounds per hour. The sulfonation liquor is intimately contacted with the extraction medium and is then passed to a separator where the insoluble hydrocarbon raffinate is removed. The extraction medium containing the sulfonic acid at 100° F. passes to the tower at which steam of 135 psig is injected into the tower bottoms. The steam heats the sulfonic acid to 214° F. As the sulfonic acid flows down the packing the isopropanol vaporizes. About 2000 pounds per hour of isopropanol and water passes overhead at 214° F. The acid with residual isopropanol and water passes out the bottom at a rate of 4600 pounds per hour. As the acid stream passes into an neutralizer, anhydrous ammonia at a rate of 135 pounds per hour also passes into the neutralizer. The ammonia rate is adjusted to provide a pH of 6-7 in the neutralized sulfonate. The product of the neutralizer at 4800 pounds per hour passes into a thin film reboiler where the product is stripped of residual isopropanol, water, ammonia and other volatiles at a temperature of 238° F. About 1400 pounds per hour of overhead vapor is collected and 3300 pounds per hour of 50% sulfonic acid in oil is produced. The overhead is returned to the tower.

Reasonable variation and modification are possible within the scope of the foregoing disclosure, drawings and claims.

I claim:

1. A method for producing ammonium hydrocarbon sulfonate which comprises (1) contacting a sulfonation liquor comprising a hydrocarbon sulfonic acid, unreacted hydrocarbon and $SO_3$ with an alcoholic extraction medium in which unreacted hydrocarbon is insoluble, (2) separating the insoluble hydrocarbon raffinate from the extraction medium, (3) removing a substantial portion of the extraction medium in a stripping tower to produce sulfonic acid having residual amounts of extraction medium, (4) neutralizing the sulfonic acid with an excess of ammonia reagent to produce an ammonium sulfonate, and heating the ammonium sulfonate to remove residual volatile materials.

2. The process of claim 1 wherein the hydrocarbon is selected from a group of hydrocarbons consisting of gas-oils, petroleum fractions, crude oils, reduced crude oils, hydrogenated gas-oils, and alkylated benzenes.

3. The process of claim 1 wherein the alcoholic extraction medium comprises about 1 part by weight of water per each 0.2 to 100 parts by weight of alcohol and the alcohol comprises a lower alkanol containing 1 to 4 carbon atoms.

4. The process of claim 3 wherein said alcohol comprises isopropanol and there is 0.5 to 2 parts by weight of water per part by weight of isopropanol in the alcoholic extraction medium.

5. The process of claim 1 wherein the solvent stripping tower is steam heated.

6. The process of claim 1 wherein the volatile material is returned to the stripping tower.

* * * * *